United States Patent
Kutsuma et al.

(10) Patent No.: US 9,781,343 B2
(45) Date of Patent: Oct. 3, 2017

(54) IMAGE PROCESSING APPARATUS AND METHOD FOR OPERATING IMAGE PROCESSING APPARATUS

(71) Applicant: OLYMPUS CORPORATION, Tokyo (JP)

(72) Inventors: Yuji Kutsuma, Kokubunji (JP); Tatsuhiko Suzuki, Hino (JP); Tomoki Iwasaki, Fuchu (JP); Susumu Hashimoto, Hachioji (JP); Toshihiro Hamada, Fuchu (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/295,085

(22) Filed: Oct. 17, 2016

(65) Prior Publication Data

US 2017/0034437 A1 Feb. 2, 2017

Related U.S. Application Data

(63) Continuation of application No. PCT/JP2015/083198, filed on Nov. 26, 2015.

(30) Foreign Application Priority Data

Dec. 2, 2014 (JP) .................. 2014-244294

(51) Int. Cl.
*H04N 7/18* (2006.01)
*H04N 5/232* (2006.01)
(Continued)

(52) U.S. Cl.
CPC ..... *H04N 5/23238* (2013.01); *A61B 1/00059* (2013.01); *A61B 1/00177* (2013.01);
(Continued)

(58) Field of Classification Search
CPC ........ H04N 5/23238; H04N 2005/2255; G06T 7/12; G06T 7/97; G06T 1/00;
(Continued)

(56) References Cited

U.S. PATENT DOCUMENTS

2002/0026274 A1* 2/2002 Morizane ........... B60K 31/0008
701/93
2013/0076879 A1* 3/2013 On ..................... A61B 1/00009
348/65
2014/0204187 A1 7/2014 Sasaki et al.

FOREIGN PATENT DOCUMENTS

EP 2762059 A1 8/2014
JP 2012-138876 A 7/2012
(Continued)

OTHER PUBLICATIONS

International Search Report dated Feb. 23, 2016 issued in PCT/JP2015/083198.

*Primary Examiner* — Allen Wong
(74) *Attorney, Agent, or Firm* — Scully, Scott, Murphy & Presser, P.C.

(57) ABSTRACT

An image processing apparatus includes a first input section configured to receive image data including images in a forward field of view and a lateral field of view; an enhancement processing section configured to enhance edges of images corresponding to the image data received; and a boundary correction section provided on a downstream side of the enhancement processing section and configured to perform a correction process non-commutative with an edge enhancement process, the correction process being performed on a boundary region between a forward field of view and a lateral field of view using the image data subjected to edge enhancement.

12 Claims, 6 Drawing Sheets

(51) Int. Cl.
*A61B 1/04* (2006.01)
*G06T 1/00* (2006.01)
*A61B 1/00* (2006.01)
*G06T 5/00* (2006.01)
*G06T 7/00* (2017.01)
*G06T 7/12* (2017.01)
*H04N 5/225* (2006.01)

(52) U.S. Cl.
CPC ............... *A61B 1/04* (2013.01); *G06T 1/00* (2013.01); *G06T 5/00* (2013.01); *G06T 7/12* (2017.01); *G06T 7/97* (2017.01); *G06T 2207/10068* (2013.01); *G06T 2207/20192* (2013.01); *H04N 2005/2255* (2013.01)

(58) Field of Classification Search
CPC . G06T 2207/10068; G06T 2207/20192; G06T 5/00; A61B 1/00059; A61B 1/00177; A61B 1/04
USPC .......................................................... 348/65
See application file for complete search history.

(56) References Cited

FOREIGN PATENT DOCUMENTS

| | | |
|---|---|---|
| JP | 2013-066646 A | 4/2013 |
| WO | WO 2013/047215 A1 | 4/2013 |

* cited by examiner

IMAGE PROCESSING APPARATUS AND METHOD FOR OPERATING IMAGE PROCESSING APPARATUS

CROSS REFERENCE TO RELATED APPLICATION

This application is a continuation application of PCT/JP2015/083198 filed on Nov. 26, 2015 and claims benefit of Japanese Application No. 2014-244294 filed in Japan on Dec. 2, 2014, the entire contents of which are incorporated herein by this reference.

BACKGROUND OF THE INVENTION

1. Field of the Invention

The present invention relates to an image processing apparatus configured to perform a correction process on a boundary region between a forward field of view and lateral field of view as well as to a method for operating the image processing apparatus.

2. Description of the Related Art

Recently, a super-wide-angle endoscope with an expanded angle of view has been proposed, such as an endoscope configured to acquire a forward-field-of-view image through a front observation window and acquire a lateral-field-of-view image through a lateral observation window.

With such an endoscope, there is a boundary region between the forward-field-of-view image and lateral-field-of-view image, and so a process of making the boundary region unobtrusive is carried out.

For example, Japanese Patent Application Laid-Open Publication No. 2013-66646 describes a technique for forming a forward-field-of-view image and lateral-field-of-view image as a front region and lateral region on a single image, performing a process of merging the images by overlaying one image over the other using an image signal of the single image, and thereby correcting a boundary region between the front region and lateral region.

SUMMARY OF THE INVENTION

An image processing apparatus according to one aspect of the present invention includes an input section configured to receive image data generated based on optical images of an object in a forward field of view and a lateral field of view; an enhancement processing section configured to perform an edge enhancement process of enhancing edges in the images in the forward field of view and the lateral field of view corresponding to the image data received by the input section, the edge enhancement process being performed on the image data; and a correction processing section provided on a downstream side of the enhancement processing section and configured to perform a correction process non-commutative with the edge enhancement process, the correction process being performed on a boundary region which is a region serving as a boundary between the image in the forward field of view and the image in the lateral field of view using the image data subjected to the edge enhancement process.

A method for operating an image processing apparatus according to one aspect of the present invention includes: a step in which an input section receives image data generated based on optical images of an object in a forward field of view and a lateral field of view; a step in which an enhancement processing section performs an edge enhancement process of enhancing edges in the images in the forward field of view and the lateral field of view corresponding to the image data received by the input section, the edge enhancement process being performed on the image data; and a step in which a correction processing section provided on a downstream side of the enhancement processing section performs a correction process non-commutative with the edge enhancement process, the correction process being performed on a boundary region which is a region serving as a boundary between the image in the forward field of view and the image in the lateral field of view using the image data subjected to the edge enhancement process.

DETAILED DESCRIPTION OF THE PREFERRED EMBODIMENT(S)

An embodiment of the present invention will be described below with reference to the drawings.

First Embodiment

Figure 1:
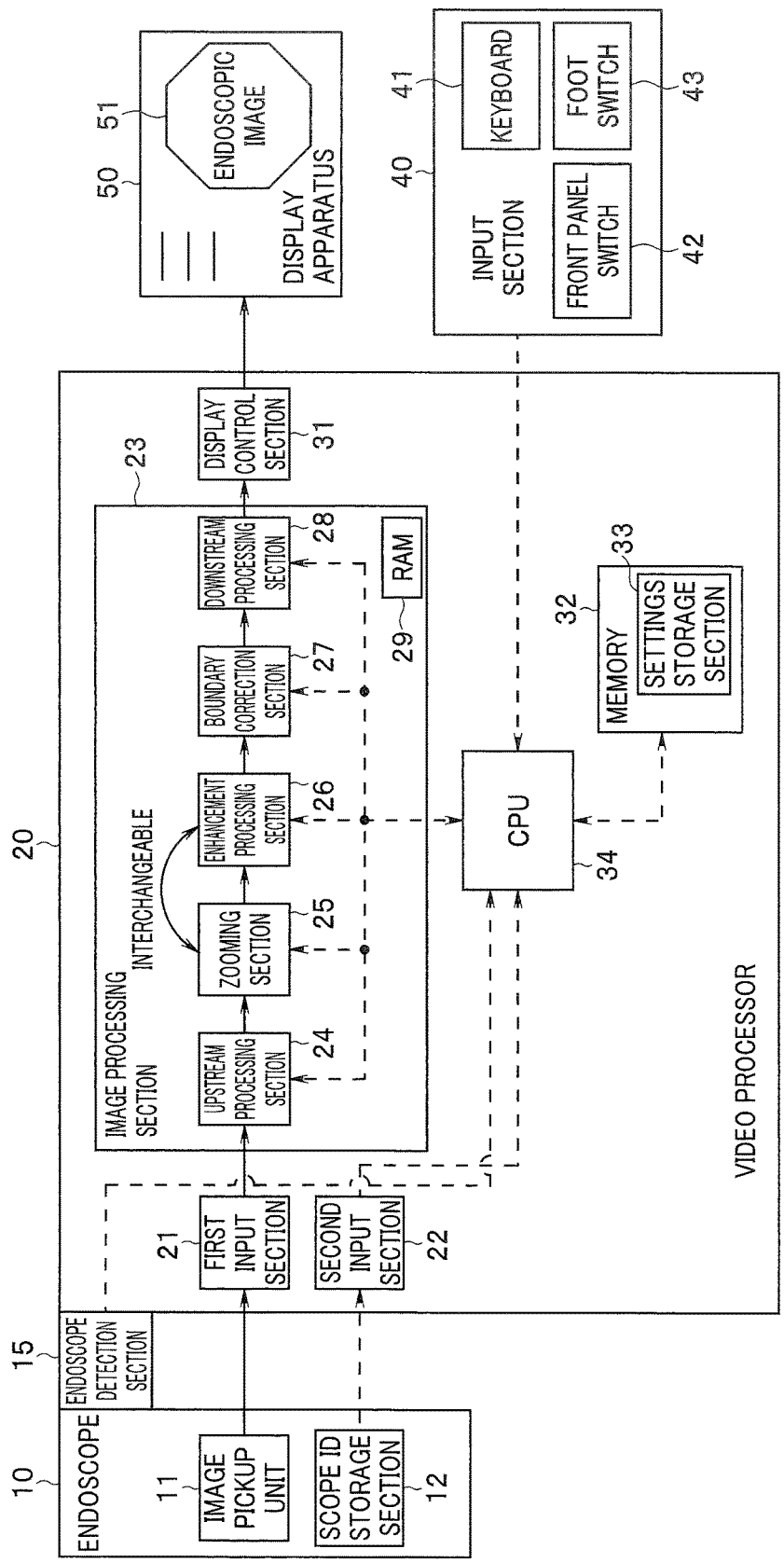
FIG. 1 is a block diagram showing a configuration of an endoscope system according to a first embodiment of the present invention.

FIGS. 1 to 10 show a first embodiment of the present invention, where FIG. 1 is a block diagram showing a configuration of an endoscope system.

The endoscope system includes an endoscope 10, which is an image pickup apparatus configured to acquire image data by picking up an image of an object, a video processor 20, which is an image processing apparatus configured to generate a display signal by processing image data outputted from the endoscope 10, an endoscope detection section 15 configured to detect a connection between the endoscope 10 and video processor 20, an input section 40 used to enter input into the endoscope system, and a display apparatus 50 configured to display an endoscopic image generated by the video processor 20.

The endoscope 10 includes an image pickup unit 11 and a scope ID storage section 12.

The image pickup unit 11 includes an objective optical system and an image pickup device. The objective optical system is configured as an optical system serving both as a direct-view optical system and a lateral-view optical system and is configured to form an optical image of an object in a forward field of view in a direct-view direction and an optical image of the object in a lateral field of view in a lateral-view direction on the image pickup device. Thus, the image pickup device outputs image data generated based on the optical images of the object in the forward field of view and lateral field of view. In this way, the endoscope 10 according to the present embodiment is constructed as a super-wide-angle endoscope configured to acquire a forward-field-of-view image and a lateral-field-of-view image.

Figure 2:
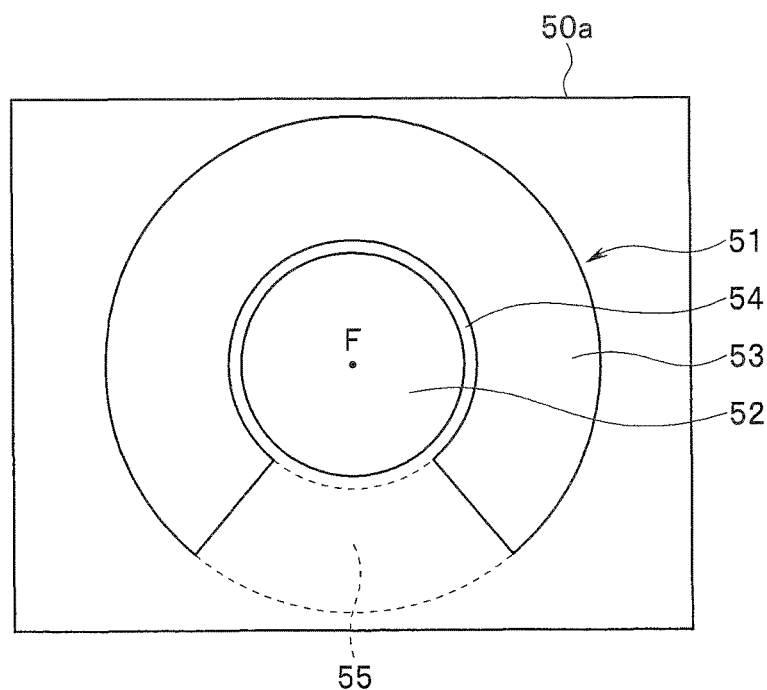
FIG. 2 is a diagram showing an example in which an image corresponding to image data outputted from an image pickup device is displayed on a screen of a display apparatus without performing a boundary correction process, in the first embodiment.

Now, FIG. 2 is a diagram showing an example in which an image corresponding to image data outputted from the image pickup device is displayed on a screen 50a of the display apparatus 50 without performing a boundary correction process.

The forward-field-of-view image 52 is shaped, for example, as a circle around a center F of a field of view and the lateral-field-of-view image 53 is formed substantially in an annular shape in an outer circumferential portion of the forward-field-of-view image 52. Here, although the lateral-field-of-view image 53 shown in FIG. 2 and the like is substantially annular, vignetting 55 occurs in part of the image in a circumferential direction under the influence of a structure disposed on a distal end face of the endoscope 10.

The boundary region 54 is between an outer circumference of the forward-field-of-view image 52 located on an inner diameter side and an inner circumferential side of the lateral-field-of-view image 53 located on an outer diameter side.

Next, the scope ID storage section 12 is designed to store unique information about the endoscope 10 in a non-volatile manner, and information is prestored during manufacture, including information about the type (model number) and serial number of the endoscope 10, the type (model number) of image pickup device provided on the endoscope 10, size and effective pixel count of the image pickup device, locations of the forward-field-of-view image 52 and lateral-field-of-view image 53 (and thus, a location of the boundary region 54) on the image pickup device. Here, the information about the location of the boundary region 54 includes at least one of, for example, information which represents an inner radius rin (see FIG. 4) of the boundary region 54 and information which represents an outer radius rout (see FIG. 4) of the boundary region 54. Specifically, a first example of the information about the location of the boundary region 54 is the information which represents the inner radius rin of the boundary region 54 and information which represents the outer radius rout of the boundary region 54 (i.e., both sets of information). Also, a second example is the information which represents the inner radius rin of the boundary region 54 and information which represents a ratio (rout/rin) of the outer radius rout to the inner radius rin of the boundary region 54. Furthermore, a third example is information which represents the outer radius rout of the boundary region 54 and information which represents a ratio (rin/rout) of the inner radius rin to the outer radius rout of the boundary region 54.

The endoscope detection section 15 is designed to detect whether or not the endoscope 10 is connected and transmit detection results to an after-mentioned CPU 34 of the video processor 20 and is made up, for example, of electrical contacts provided on both the endoscope 10 and video processor 20, a sensor provided on the video processor 20.

The video processor 20 is an image processing apparatus provided with a first input section 21, a second input section 22, an image processing section 23, a display control section 31, a memory 32, and a CPU 34 and is designed to receive image data and perform image processing.

The first input section 21 receives the image data generated by the image pickup unit 11 based on the optical images of the object in the forward field of view and lateral field of view.

The second input section 22 receives the above-mentioned unique information about the endoscope 10, which is the image pickup apparatus that has acquired the image data.

The image processing section 23 is designed to perform image processing on the image data inputted via the first input section 21 and is provided with an upstream processing section 24, a zooming section 25, an enhancement processing section 26, a boundary correction section 27, a downstream processing section 28, and a RAM 29.

The upstream processing section 24 performs various processes such as gain adjustment, defective pixel correction, and white balance adjustment on inputted image data.

The zooming section 25, which is provided on an upstream side of the boundary correction section 27, is a scaling section configured to perform a scaling process (zoom-in process or zoom-out process), which is so-called electronic zooming, on image data in the forward field of view and lateral field of view.

The enhancement processing section 26 performs an edge enhancement process on the image data inputted via the first input section 21, where the edge enhancement process enhances edges (outline) of the images in the forward field of view and lateral field of view corresponding to the image data. Here, the edge enhancement process extracts an edge component, for example, by applying an edge detection filter to the image data, multiplies the extracted edge component by an edge enhancement coefficient $\alpha$ and adds the product to the original image data. Thus, an edge enhancement level, which is intensity of the edge enhancement process, is adjusted, for example, by changing a value of the edge enhancement coefficient $\alpha$.

The boundary correction section 27, which is provided on a downstream side of the enhancement processing section 26, is a boundary correction processing section (correction processing section) adapted to perform a boundary correction process (correction process) on the boundary region 54 which is a region serving as a boundary between the forward-field-of-view image 52 and lateral-field-of-view image 53 using the image data subjected to the edge enhancement process and thereby makes the boundary region unobtrusive.

Here, the boundary correction process performed by the boundary correction section 27 is non-commutative with the edge enhancement process described above. That is, suppose P denotes image data, $E_{(\ )}$ denotes a function which represents an edge enhancement process, $B_{(\ )}$ denotes a function which represents a boundary correction process, "·" is a symbol which indicates a composite function, P' denotes a processing result obtained when the edge enhancement process $E_{(\ )}$ is performed prior to the boundary correction process $B_{(\ )}$, and P" denotes a processing result obtained when the boundary correction process $B_{(\ )}$ is performed prior to the edge enhancement process $E_{(\ )}$. Now, if $$P'=B(E(P))\equiv B \cdot E(P)$$

and $$P''=E(B(P))\equiv E \cdot B(P)$$

differ from each other (P'≠P"), i.e., if B·E≠E·B, then it is said that the boundary correction process $B_{(\ )}$ and edge enhancement process $E_{(\ )}$ are non-commutative with each other.

Figure 3:
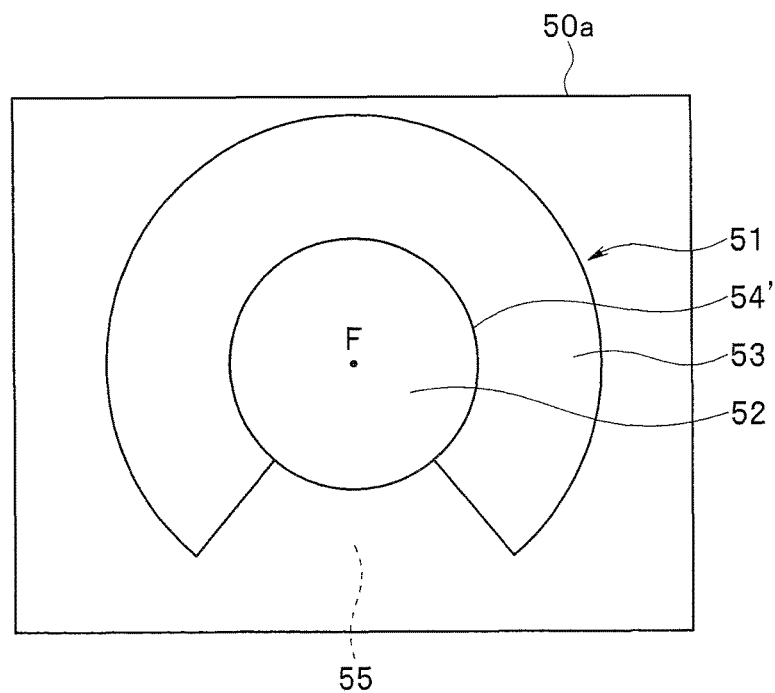
FIG. 3 is a diagram showing an example in which an image corresponding to image data outputted from the image pickup device is displayed on the screen of the display apparatus by performing a boundary correction process, in the first embodiment.

An example of the boundary correction process performed by the boundary correction section 27 is an overlap process such as shown in FIG. 3. FIG. 3 is a diagram showing an example in which an image corresponding to the image data outputted from the image pickup device is displayed on the screen 50a of the display apparatus 50 by performing a boundary correction process.

The overlap process involves enlarging at least one of the forward-field-of-view image 52 and lateral-field-of-view image 53 and thereby covering (overlapping) the boundary region 54 with the enlarged forward-field-of-view image 52 or lateral-field-of-view image 53. The fact that the overlap process is non-commutative with the edge enhancement process $E_{(\ )}$ will be described later with reference to FIGS. 4 to 9.

The downstream processing section 28 performs various processes such as gray scale conversion, color space conversion, and gamma correction on image data.

The RAM 29 is a memory configured to temporarily store the image data processed by the image processing section 23.

The display control section 31 superimposes character information and the like about the endoscope system on the image data subjected to image processing by the image processing section 23, converts the data into a display signal, and outputs the signal to the display apparatus 50.

The memory 32 stores a processing program executed by the CPU 34 and includes a settings storage section 33 configured to store various settings specified for the endoscope system. The settings storage section 33 stores unique information about the endoscope 10 (information about the type of the endoscope 10, type of image pickup device, effective pixel count of the image pickup device, and the like) read out of the scope ID storage section 12 as well as information about a zoom factor (scaling factor), edge enhancement level, boundary correction range, and the like inputted via the input section 40 described later.

The CPU 34 is a control section configured to control the entire endoscope system, including the video processor 20, in an integrated manner The CPU 34 is designed to function as a boundary correction range setting section, an enhancement level setting section, a scaling factor setting section, and the like as well.

That is, functioning as an enhancement level setting section, the CPU 34 sets the intensity (edge enhancement level) of the edge enhancement process performed by the enhancement processing section 26. Here, the CPU 34 sets the edge enhancement level on the enhancement processing section 26, for example, based on the edge enhancement level set as an initial value, based on automatic processing on results of image analysis, or, further, based on a manual input via the input section 40. Then, based on the set edge enhancement level, the CPU 34 functioning as the boundary correction range setting section, sets a range (width of the boundary region 54 in a radial direction around the center F of the field of view, for example, as shown in FIG. 2) of the boundary region 54 in which the boundary correction section 27 performs a boundary correction process.

Also, functioning as a scaling factor setting section, the CPU 34 sets a scaling factor for a scaling process performed by the zooming section 25. Here, the CPU 34 sets the scaling factor on the zooming section 25, for example, based on the scaling factor set as an initial value or based on input settings from the input section 40. Then, based on the set scaling factor, the CPU 34 functioning as the boundary correction range setting section sets the range of the boundary region 54 in which the boundary correction section 27 performs the boundary correction process.

Furthermore, based on the unique information acquired from the second input section 22, the CPU 34 functioning as the boundary correction range setting section set the range of the boundary region 54 in which the boundary correction section 27 performs the boundary correction process.

The input section 40 is equipped with various input devices such as a keyboard 41, a front panel switch 42, a foot switch 43 and is connected to the CPU 34. The input section 40 allows various settings and inputs to be entered with respect to the endoscope system, and examples of some input settings include the zoom factor (scaling factor) of electronic zooming specified via the zooming section 25, the edge enhancement level specified to the enhancement processing section 26 (the edge enhancement level determines the edge enhancement coefficient α), and the boundary correction range set by the boundary correction section 27.

The display apparatus 50 includes an endoscopic image display section 51 configured to display image data picked up by the endoscope 10 and moreover, displays various information and the like on the endoscope system.

Next, the fact that the overlap process and edge enhancement process are non-commutative with each other will be described with reference to FIGS. 4 to 9.

Figure 4:
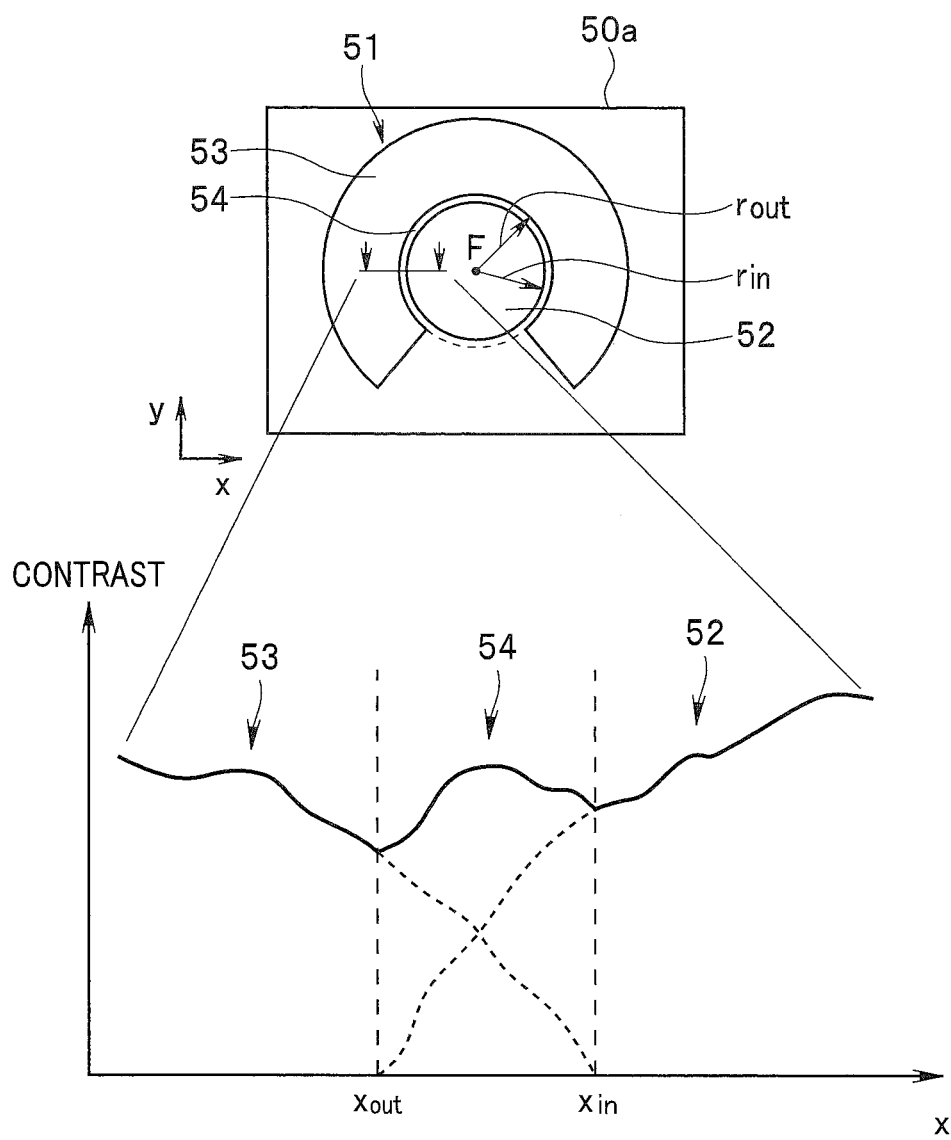
FIG. 4 is a diagram showing an example of changes in an image and signal values when image data yet to undergo an overlap process and edge enhancement process is displayed on the screen of the display apparatus, in the first embodiment.

First, FIG. 4 is a diagram showing an example of changes in an image and signal values when image data yet to undergo an overlap process and edge enhancement process is displayed on the screen 50a of the display apparatus 50.

As shown in the top diagram of FIG. 4, the forward-field-of-view image 52 is a circular region centered at the center F of the field of view and located within the radius rin while the lateral-field-of-view image 53 is a substantially annular region centered at the center F of the field of view and located outside the radius rout (rout >rin). Then, a region which satisfies rin≤r≤rout is the boundary region 54 (thus, the boundary region 54 has an inner radius of rin and an outer radius of rout).

An example of changes in a signal value (e.g., contrast) on opposite sides of the boundary region 54 is shown in the bottom diagram of FIG. 4. Note that in the top diagram of FIG. 4, x-y coordinate axes are set by assuming that the horizontal right direction corresponds to a positive x coordinate direction while the vertical upward direction corresponds to a positive y coordinate direction.

When an x coordinate xin corresponding to the radius rin is exceeded (in a negative x coordinate direction in the case of the present coordinate setting), a value of contrast due to the forward-field-of-view image 52 falls rapidly because of rapid decreases in a light quantity of object light through the forward field of view.

Similarly, when an x coordinate xout corresponding to the radius rout is exceeded (in a positive x coordinate direction in the case of the present coordinate setting), a value of contrast originating in the lateral-field-of-view image 53 falls rapidly because of rapid decreases in a light quantity of object light through the lateral field of view.

Then, in the boundary region 54, contrast originating in the forward-field-of-view image 52 and contrast originating in the lateral-field-of-view image 53 are superimposed on each other, forming a contrast distribution such as illustrated.

Note that in the example shown here, the forward-field-of-view image 52 and lateral-field-of-view image 53 are connected in the boundary region 54 relatively smoothly in terms of contrast, there is a case in which the contrast in the boundary region 54 is reduced to almost zero depending on a configuration of the objective optical system and the like.

Figure 5:
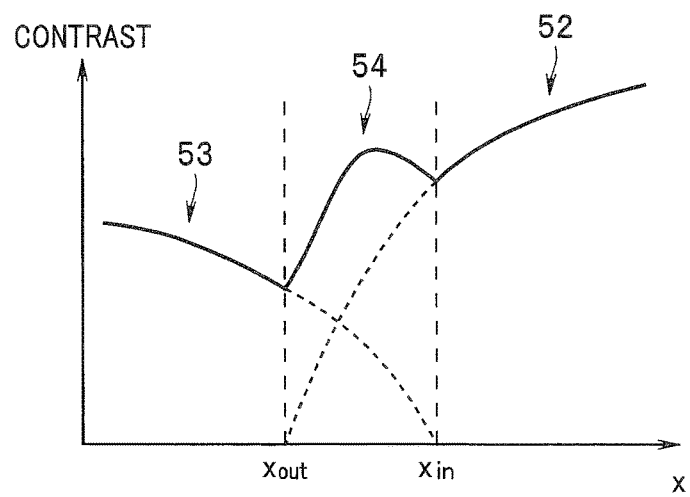
FIG. 5 is a chart which models the signal value changes of FIG. 4 in the first embodiment.

Next, FIG. 5 is a chart which models the signal value changes of FIG. 4. Although a curved shape is modeled into a simplified shape, the contrast at the x coordinate xin of the forward-field-of-view image 52 and the contrast at the x coordinate xout of the lateral-field-of-view image 53 have different values.

Figure 6:
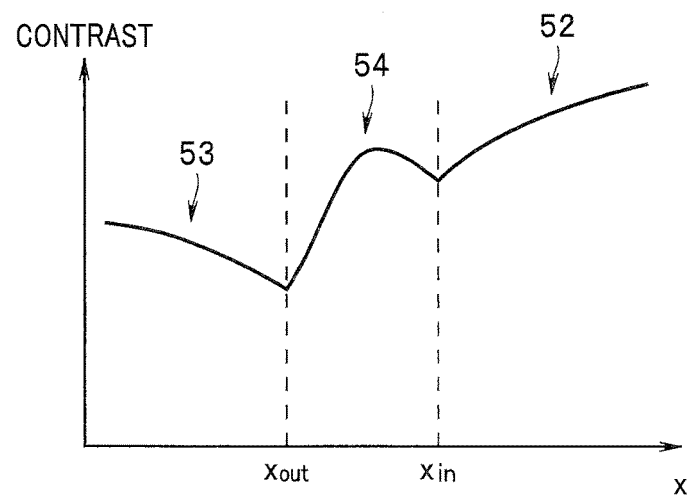
FIG. 6 is a chart showing a state which results when an edge enhancement process is performed on image data having a contrast distribution shown in FIG. 5, in the first embodiment.

Next, FIG. 6 is a chart showing a state which results when an edge enhancement process is performed on image data having a contrast distribution shown in FIG. 5.

In the contrast distribution shown in FIG. 5, there is almost no edge portion with sudden contrast changes, and so the edge enhancement process has not changed the image data very much.

Figure 7:
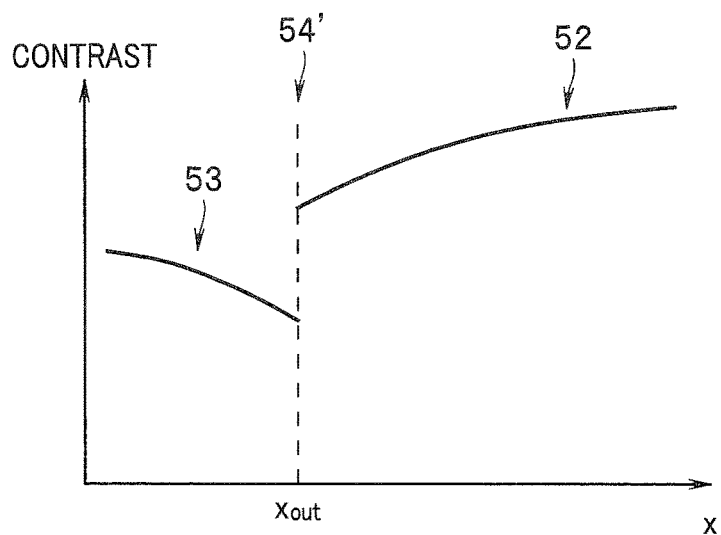
FIG. 7 is a chart showing a state which results when a boundary correction process is performed on image data having a contrast distribution shown in FIG. 6, in the first embodiment.

FIG. 7 is a chart showing a state which results when a boundary correction process is performed on image data having a contrast distribution shown in FIG. 6.

The boundary correction process here is performed, for example, by an overlap process in which the forward-field-of-view image 52 is enlarged and connected to the lateral-field-of-view image 53. Consequently, the boundary region 54 having a width in FIGS. 5 and 6 is reduced to just a boundary line 54' after the boundary correction process.

Figure 8:
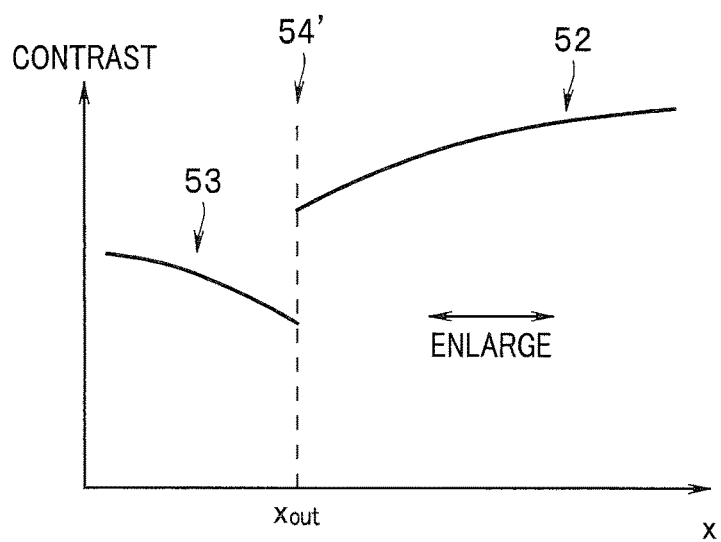
FIG. 8 is a chart showing a state which results when a boundary correction process is performed on image data having the contrast distribution shown in FIG. 5, in the first embodiment.

On the other hand, FIG. 8 is a chart showing a state which results when a boundary correction process is performed on image data having the contrast distribution shown in FIG. 5.

Almost as with the example shown in FIG. 7, when the overlap process is performed as a boundary correction process, the boundary region 54 having a width in FIGS. 5 and 6 is reduced to just a boundary line 54' after the boundary correction process. Then, as described above, since the contrast at the x coordinate xin of the forward-field-of-view image 52 and the contrast at the x coordinate xout of the lateral-field-of-view image 53 have different values, an edge, i.e., a portion in which the contrast changes suddenly, is produced on the boundary line 54'.

Figure 9:
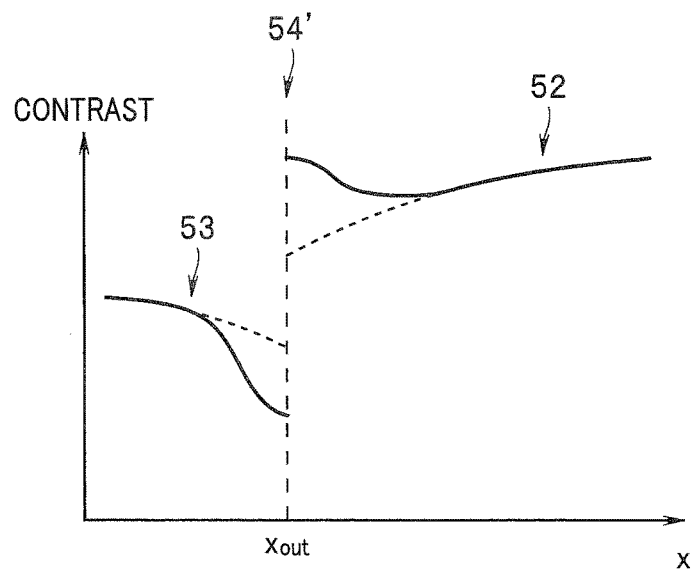
FIG. 9 is a chart showing a state which results when an edge enhancement process is performed on image data having a contrast distribution shown in FIG. 8, in the first embodiment.

FIG. 9 is a chart showing a state which results when an edge enhancement process is performed on image data having a contrast distribution shown in FIG. 8.

In edge enhancement process, since the contrast gap in the edge portion is enlarged, on opposite sides of the boundary line 54', the originally high contrast on the side of the forward-field-of-view image 52 is increased further while the originally low contrast on the side of the lateral-field-of-view image 53 is reduced further.

In this way, processing results shown in FIG. 7 produced by first performing the edge enhancement process and then performing the boundary correction process and processing results shown in FIG. 9 produced by first performing the boundary correction process and then performing the edge enhancement process differ from each other, that is, it can be seen that the edge enhancement process and boundary correction process are non-commutative with each other.

Moreover, as shown in FIG. 9, when the boundary correction process is performed first followed by the edge enhancement process the edge produced by the boundary correction process is enhanced, and consequently the boundary between the forward-field-of-view image 52 and lateral-field-of-view image 53 becomes more noticeable.

Thus, as shown in FIG. 1, the present embodiment adopts a configuration in which the boundary correction section 27 is placed on the downstream side of the enhancement processing section 26. This makes it possible to inhibit the edge produced on the boundary line 54' from being enhanced as shown in FIG. 7.

Furthermore, in the present embodiment, as shown in FIG. 1, the zooming section 25 is placed on the upstream side of the boundary correction section 27. This is because if the scaling process is performed after the boundary correction process, even though the boundary region 54 shown in FIG. 2 is reduced by the boundary correction process to the boundary line 54' shown in FIG. 3, the boundary line 54' is enlarged again by a subsequent scaling process (zoom-in process), becoming noticeable as the boundary region 54.

Note that as long as the condition that the zooming section 25 and enhancement processing section 26 are placed on the upstream side of the boundary correction section 27 is satisfied, the order of the zooming section 25 and enhancement processing section 26 may be changed as shown in FIG. 1. This is not limited to the zooming section 25 and enhancement processing section 26, and if the boundary line 54' obtained when the boundary region 54 is corrected by the boundary correction section 27 subsequently becomes noticeable as a result of some process, preferably a processing section which performs the process is placed on the upstream side of the boundary correction section 27.

Also, for example, if the forward-field-of-view image 52 and lateral-field-of-view image 53 are connected smoothly to each other in the boundary region 54 and the boundary region 54 looks less awkward as it is, it is conceivable to reduce a scope of the boundary correction process. Alternatively, as described with reference to FIG. 7, since the boundary correction process, if performed, will cause a gap to be produced in the image contrast and observed as an edge, it is thought that the boundary correction process had better not be performed.

Thus, as partly explained above, the following processes are performed.

That is, if the edge enhancement process is performed, the contrast gap in the edge is enlarged, making the boundary noticeable as described above. Thus, when the intensity of the edge enhancement process performed by the enhancement processing section 26 is high, the CPU 34, which functions as the boundary correction range setting section, increases the range of the boundary region 54 in which the boundary correction section 27 performs the boundary correction process, and conversely when the intensity of the edge enhancement process performed by the enhancement processing section 26 is low, the CPU 34 decreases the range of the boundary region 54.

Figure 10:
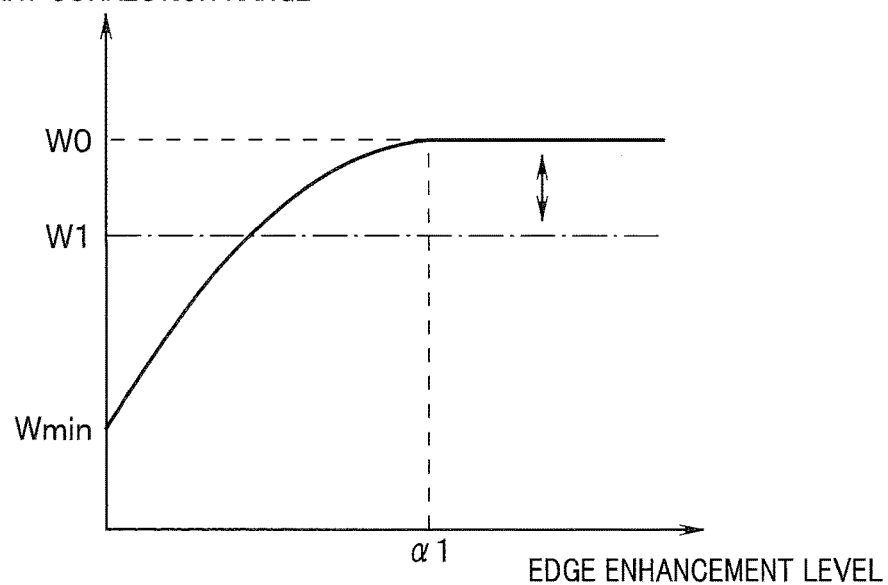
FIG. 10 is a chart showing an example of a boundary correction range set on an edge enhancement level, in the first embodiment.

FIG. 10 is a chart showing an example of the boundary correction range set on the edge enhancement level.

In FIG. 10, the edge enhancement coefficient α described above is used as an index which represents the intensity (edge enhancement level) of the edge enhancement process.

As illustrated, when edge enhancement level is the lowest (e.g., when the edge enhancement level is 0 and no edge enhancement is performed), the boundary correction range takes a minimum range of Wmin. Here, the boundary correction range W according to the present embodiment is assumed to be (but not limited to) the width of the boundary region 54 which is subjected to the boundary correction process and located in the radial direction around the center F of the field of view shown in FIG. 2 and other drawings. Then, the boundary correction range W expands with increases in the edge enhancement coefficient $\alpha$ configured to represent the edge enhancement level, and takes a maximum value of W0 when the edge enhancement coefficient $\alpha$ reaches a certain value $\alpha 1$. The maximum value of W0 is maintained even when the edge enhancement coefficient $\alpha$ exceeds the value $\alpha 1$.

Also, when an image is enlarged by the zooming section 25, the enlarged image decreases in sharpness. To deal with this, the edge enhancement level is set high. That is, there is a positive relationship between the scaling factor of the scaling process and the edge enhancement level. Thus, when the scaling factor of the scaling process performed by the zooming section 25 is large (i.e., when the edge enhancement level is high), the CPU 34, which functions as the boundary correction range setting section, makes settings to increase the range of the boundary region 54 in which the boundary correction section 27 performs the boundary correction process, and conversely when the scaling factor is small (i.e., when the edge enhancement level is low), the CPU 34 makes settings to decrease the range of the boundary region 54 (e.g., changes the boundary correction range setting from W0 to W1 shown in FIG. 10).

Furthermore, for example, if the endoscope 10 has a small diameter a small image pickup device is used, but a small image pickup device has a low pixel count, and so a zoom-in process is sometimes performed to display the image on the display apparatus 50. Also, a lot of noise may be generated at low luminance depending on the type of image pickup device, and such noise is reduced using interpolation from surrounding pixels. Thus, a process, such as a zoom-in process or noise reduction process, which involves pixel interpolation reduces image sharpness, and the edge enhancement level may be set high as with the above case to deal with this problem. Thus, functioning as the boundary correction range setting section, the CPU 34 sets the range of the boundary region 54 in which the boundary correction section 27 performs the boundary correction process, based on the unique information (information about the type of the endoscope 10, type of image pickup device, effective pixel count of the image pickup device, and the like) acquired from the second input section 22. As a specific example, the CPU 34 makes settings to decrease the range of the boundary region 54 when the effective pixel count of the image pickup device is high and makes settings to increase the range of the boundary region 54 (e.g., changes the maximum value setting of the boundary correction range from W0 to W1 shown in FIG. 10) when the effective pixel count of the image pickup device is low.

Note that the range of the boundary region 54 in which the boundary correction section 27 performs the boundary correction process (boundary correction range) can be set manually by a user via the input section 40 as described above. In this case, the user can make desired settings to obtain an optimum display while observing the image displayed on the endoscopic image display section 51 of the display apparatus 50.

According to the first embodiment, configured as described above, since the boundary correction section 27 configured to perform the boundary correction process non-commutative with the edge enhancement process is provided on the downstream side of enhancement processing section 26, the edge produced on the boundary between the forward-field-of-view image 52 and lateral-field-of-view image 53 by the boundary correction process is not enhanced by the edge enhancement process. This provides an image in which the boundary region 54 between the forward field of view and lateral field of view has been corrected properly.

Also, since the boundary correction section 27 is designed to perform the overlap process as the boundary correction process non-commutative with the edge enhancement process, the boundary region 54 can be made less noticeable using a relatively simple process.

Furthermore, since the zooming section 25 configured to perform the scaling process on the image is provided on the upstream side of the boundary correction section 27, the edge produced on the boundary between the forward-field-of-view image 52 and lateral-field-of-view image 53 by the boundary correction process is not enlarged in area by the scaling process. This provides an image in which the boundary region 54 between the forward field of view and lateral field of view has been corrected properly.

Then, since the CPU 34 functioning as the boundary correction range setting section is designed to set the range of the boundary region 54 in which the boundary correction section 27 performs the boundary correction process, boundary correction can be made in an appropriate range as required.

In addition, since the CPU 34 is designed to set the range of the boundary region 54 for the boundary correction process based on the intensity of the edge enhancement process, the boundary correction process can be performed in an appropriate range according to the edge enhancement level.

In so doing, the range of the boundary region 54 for the boundary correction process can also be set appropriately based on the scaling factor of the scaling process which affects the intensity of the edge enhancement process.

Besides, the range of the boundary region 54 for the boundary correction process can also be set appropriately based on the unique information about the endoscope 10 (information about the type of the endoscope 10, type of image pickup device, effective pixel count of the image pickup device, and the like) which affects the intensity of the edge enhancement process.

In so doing, at least one of information which represents the inner radius rin of the boundary region 54 and information which represents the outer radius rout of the boundary region 54 is included as information about the location of the boundary region 54. Specifically, using the information which represents the inner radius rin of the boundary region 54 and information which represents the outer radius rout of the boundary region 54, using the information which represents the inner radius rin of the boundary region 54 and information about the ratio (rout/rin) of the outer radius rout to the inner radius rin of the boundary region 54, or using the information which represents the outer radius rout of the boundary region 54 and information about the ratio (rin/rout) of the inner radius rin to the outer radius rout of the boundary region 54, the location of the boundary region 54 can be expressed accurately with a small amount of data.

Note that whereas mainly an image processing apparatus has be described above, the present invention is also applicable to an operation method configured to operate the image processing apparatus as described above, a processing program configured to perform operation similar to the image processing apparatus, a computer-readable, non-temporary recording medium configured to store the processing program, and so on.

Also, the present invention is not limited to the precise embodiment described above and may be embodied by changing components in the implementation stage without departing from the spirit of the invention. Also, various aspects of the invention can be formed using appropriate combinations of the components disclosed in the above embodiment. For example, some of the components disclosed in the embodiment may be deleted. Furthermore, components may be combined as required across different embodiments. Thus, needless to say that various alterations and applications are possible without departing from the spirit of the invention.

What is claimed is:

1. An image processing apparatus comprising:
a processor comprising hardware, wherein the processor is configured to:
receive image data generated based on optical images of an object in a forward field of view and a lateral field of view;
perform an edge enhancement process of enhancing edges in the images in the forward field of view and the lateral field of view corresponding to the image data received, the edge enhancement process being performed on the image data; and
perform, on a downstream side of the edge enhancement process, a correction process non-commutative with the edge enhancement process, the correction process being performed on a boundary region which is a region serving as a boundary between the image in the forward field of view and the image in the lateral field of view using the image data subjected to the edge enhancement process.

2. The image processing apparatus according to claim 1, wherein as the correction process non-commutative with the edge enhancement process, the processor is configured to perform an overlap process of causing at least one of the image in the forward field of view and the image in the lateral field of view to overlap the boundary region.

3. The image processing apparatus according to claim 1, wherein the processor is configured to perform, on an upstream side of the correction process, a scaling process on the images in the forward field of view and the lateral field of view.

4. The image processing apparatus according to claim 1, wherein the processor is configured to set a range of the boundary region in which the correction process is performed.

5. The image processing apparatus according to claim 4, wherein the processor is configured to: set intensity of the edge enhancement process performed; set the range of the boundary region in which the correction process is performed, based on the intensity of the edge enhancement process set.

6. The image processing apparatus according to claim 4, wherein the processor is configured to: perform, on an upstream side of the correction process, a scaling process on the images in the forward field of view and the lateral field of view;
set a scaling factor for the scaling process performed; and
set the range of the boundary region in which the correction process is performed, based on the scaling factor set.

7. The image processing apparatus according to claim 4, wherein the processor is configured to: receive unique information about an image pickup apparatus acquiring the image data; and set the range of the boundary region in which the correction process is performed, based on the unique information.

8. The image processing apparatus according to claim 7, wherein the unique information includes information about a location of the boundary region.

9. The image processing apparatus according to claim 8, wherein the information about the location of the boundary region includes at least one of information about an inner radius of the boundary region and information about an outer radius of the boundary region.

10. The image processing apparatus according to claim 9, wherein the information about the location of the boundary region includes the information about the inner radius of the boundary region and information about a ratio of the outer radius to the inner radius of the boundary region.

11. The image processing apparatus according to claim 9, wherein the information about the location of the boundary region includes information about the outer radius of the boundary region and information about a ratio of the inner radius to the outer radius of the boundary region.

12. A method for operating an image processing apparatus comprising:
a step in which a processor comprising hardware receives image data generated based on optical images of an object in a forward field of view and a lateral field of view;
a step in which the processor performs an edge enhancement process of enhancing edges in the images in the forward field of view and the lateral field of view corresponding to the image data received, the edge enhancement process being performed on the image data; and
a step in which the processor performs, on a downstream side of the edge enhancement process, a correction process non-commutative with the edge enhancement process, the correction process being performed on a boundary region which is a region serving as a boundary between the image in the forward field of view and the image in the lateral field of view using the image data subjected to the edge enhancement process.

* * * * *